US011376574B2

(12) United States Patent
Lee et al.

(10) Patent No.: US 11,376,574 B2
(45) Date of Patent: Jul. 5, 2022

(54) CATALYST FOR CONVERTING ALKYLAROMATIC HYDROCARBON AND PREPARATION METHOD THEREOF

(71) Applicant: SK Innovation Co., Ltd., Seoul (KR)

(72) Inventors: Sang Il Lee, Daejeon (KR); Ji Hoon Lee, Daejeon (KR); Young Eun Cheon, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 17/117,358

(22) Filed: Dec. 10, 2020

(65) Prior Publication Data

US 2021/0178372 A1 Jun. 17, 2021

(30) Foreign Application Priority Data

Dec. 17, 2019 (KR) ........................ 10-2019-0168765

(51) Int. Cl.

| | |
|---|---|
| ***B01J 29/80*** | (2006.01) |
| ***C07C 4/18*** | (2006.01) |
| ***C07C 6/12*** | (2006.01) |
| ***B01J 29/22*** | (2006.01) |
| ***B01J 29/26*** | (2006.01) |
| ***B01J 29/44*** | (2006.01) |
| ***B01J 29/48*** | (2006.01) |
| ***B01J 29/78*** | (2006.01) |
| ***B01J 37/04*** | (2006.01) |
| ***B01J 37/08*** | (2006.01) |
| *B01J 29/06* | (2006.01) |

(52) U.S. Cl.

CPC ............... *B01J 29/80* (2013.01); *B01J 29/22* (2013.01); *B01J 29/26* (2013.01); *B01J 29/44* (2013.01); *B01J 29/48* (2013.01); *B01J 29/7869* (2013.01); *B01J 37/04* (2013.01); *B01J 37/088* (2013.01); *C07C 4/18* (2013.01); *C07C 6/126* (2013.01); *B01J 2029/062* (2013.01); *C07C 2529/22* (2013.01); *C07C 2529/26* (2013.01); *C07C 2529/44* (2013.01); *C07C 2529/48* (2013.01); *C07C 2529/78* (2013.01); *C07C 2529/80* (2013.01)

(58) Field of Classification Search

CPC ... B01J 29/06; B01J 29/18; B01J 29/22; B01J 29/26; B01J 29/40; B01J 29/44; B01J 29/48; B01J 29/7869; B01J 29/80; B01J 37/0009; B01J 37/0201; B01J 37/04; B01J 37/088; B01J 2029/062; B01J 23/28; B01J 23/626; B01J 27/045; B01J 27/051; B01J 37/16; B01J 37/20; C07C 4/04; C07C 4/06; C07C 4/18; C07C 6/123; C07C 6/126; C07C 2523/28; C07C 2523/38; C07C 2527/10; C07C 2531/16; C07C 5/274; C07C 2/66; C07C 2529/22; C07C 2529/26; C07C 2529/44; C07C 2529/48; C07C 2529/78; C07C 2529/80; Y02P 20/52; C10G 35/095; C10G 2400/30

See application file for complete search history.

(56) References Cited

U.S. PATENT DOCUMENTS

| | | | | |
|---|---|---|---|---|
| 6,114,592 | A * | 9/2000 | Gajda | C07C 15/08 585/475 |
| 6,518,472 | B1 | 2/2003 | Feinstein et al. | |
| 6,867,340 | B2 * | 3/2005 | Oh | B01J 37/0009 585/475 |
| 8,481,795 | B2 | 7/2013 | Boldingh et al. | |
| 2003/0099583 | A1 | 5/2003 | Ikeda et al. | |
| 2007/0049780 | A1 | 3/2007 | Schwartz et al. | |
| 2012/0116139 | A1 | 5/2012 | Inui et al. | |
| 2015/0166434 | A1 | 6/2015 | Ward | |

FOREIGN PATENT DOCUMENTS

| | | | |
|---|---|---|---|
| KR | 1020080046691 | A | 5/2008 |
| WO | 9805613 | A1 | 2/1998 |
| WO | 0038834 | A1 | 7/2000 |

OTHER PUBLICATIONS

Baerlocher et al., Atlas of Zeolite Framework Types, 2001, 308 pages, 5th Edition, Elsevier, Amsterdam.

* cited by examiner

*Primary Examiner* — Youngsul Jeong
*Assistant Examiner* — Jason Y Chong
(74) *Attorney, Agent, or Firm* — The Webb Law Firm

(57) ABSTRACT

Disclosed are a bifunctional catalyst and a preparation method therefor, the bifunctional catalyst being suitable to produce high-value aromatic hydrocarbons by subjecting alkylaromatic hydrocarbons to a disproportionation/transalkylation/dealkylation reaction while suppressing aromatic loss or subjecting C8 aromatic hydrocarbons to an isomerization reaction while suppressing xylene loss.

11 Claims, No Drawings

CATALYST FOR CONVERTING ALKYLAROMATIC HYDROCARBON AND PREPARATION METHOD THEREOF

CROSS-REFERENCE TO RELATED APPLICATION

This application claims priority to Korean Patent Application No. 10-2019-0168765 filed Dec. 17, 2019, the disclosure of which is hereby incorporated by reference in its entirety.

BACKGROUND OF THE INVENTION

1. Field of the Invention

The present disclosure relates to a catalyst for converting an aromatic hydrocarbon and a preparation method thereof. More specifically, the present disclosure relates to a bifunctional catalyst suitable to produce a high-value aromatic hydrocarbon by subjecting an alkylaromatic hydrocarbon to a disproportionation/transalkylation/dealkylation while suppressing aromatic loss, or by subjecting C8 aromatic hydrocarbons to isomerization while suppressing xylene loss; and a method for preparing the catalyst.

2. Description of the Prior Art

C8 aromatic hydrocarbons, specifically mixed xylene (or xylene isomers), account for a large proportion in the feed sources of basic chemicals in the petrochemical field. Mixed xylene typically contains meta-xylene (m-xylene), para-xylene (p-xylene), and ortho-xylene (o-xylene). Among them, para-xylene is a raw material for the synthesis of terephthalic acid that is used for manufacturing synthetic fabric fibers and resins and o-xylene serves as a raw material for the preparation of phthalic anhydrides. On the other hand, m-xylene is used in plasticizers, azo dyes, etc. Similar boiling points among the xylene isomers make it difficult to separate particular xylenes from mixed xylenes by typical distillation. Instead, adsorption separation, crystallization, and isomerization are mainly employed for the separation and recovery of individual xylenes.

Largely, commercial preparation of mixed xylenes is achieved by separation and recovery from mixed xylene-rich fractions or by synthesis through reactions.

Representative of the former are a method in which mixed xylenes are separated through distillation of reformates obtained by catalytic reforming of naphtha and a method in which mixed xylenes are separated from pyrolysis oil generated as byproducts upon naphtha thermal cracking. However, the mixed xylene-rich fractions obtained by catalytic reforming or thermal cracking are not composed of isomers at ratios suitable for meeting the market demand. The latter is generally accompanied with reactions in which aromatic hydrocarbons are converted to xylene in the presence of a catalyst, which is typically capable of disproportionation of toluene, transalkylation of toluene/C9 aromatic compounds, dealkylation of C9+ alkyl aromatic compounds, and/or alkylation of toluene by methanol.

Typically, a reaction under hydrogen supply is involved in order to produce high-value aromatic hydrocarbons (specifically, C8 aromatics, more specifically xylenes, most specifically p-xylene) from monocyclic aromatic hydrocarbons or alkylaromatic hydrocarbons, such as benzene, toluene, and/or C9+ aromatic hydrocarbons.

Conventionally known transalkylation catalysts or C8 isomerization catalysts are mainly in the form in which hydrogenation metals are supported on zeolite, for example, zeolite having a 10-membered ring (MFI typed zeolite) and/or zeolite having a 12-member ring (MOR typed zeolite, beta-zeolite, or the like), and in order to prepare catalysts in the form of a shaped material suitable for commercialization, a binder of a porous inorganic oxide, such as alumina, silica, silica-alumina, or aluminum phosphate, is used (for example, Korean Patent Publication No. 2008-46691, U.S. Pat. No. 8,481,795, and US Patent Publication No. 2012-0116139).

However, due to increased demands to improve yields and reduce operating costs of high-value aromatic hydrocarbon products, a catalyst is required that has excellent conversion activity of alkylaromatic compounds compared with the conventional catalysts and can increase the yields of high-value aromatic hydrocarbon products through the suppression of aromatic loss or xylene loss during the reaction.

SUMMARY OF THE INVENTION

An aspect of the present disclosure is to provide a catalyst for converting aromatic hydrocarbons and a preparation method therefor, the catalyst being capable of providing favorable catalytic activity in disproportionation/transalkylation/dealkylation for producing C8 aromatic hydrocarbons (specifically xylenes) from aromatic hydrocarbons or xylene isomerization for increasing the content of a particular xylene isomer, for example, para-xylene, in C8 aromatic hydrocarbons while effectively suppressing aromatic loss or xylene loss.

Another aspect of the present disclosure is to provide a process for producing a target product at a high yield in a conversion of C6, C7, and/or C9+ aromatics into C8 aromatics (specifically mixed xylenes) or a conversion of C8 aromatics into para-xylene by using a catalyst with improved characteristics.

In accordance with an aspect of the present disclosure, there is provided a method for preparing a catalyst for converting aromatic hydrocarbons, the method comprising:

a) supporting a precursor of a first metal having hydrogenation activity on a refractory inorganic oxide binder to prepare a first metal precursor-supported binder;

b) combining a first zeolite and/or a second zeolite with the first metal precursor-supported binder, to prepare a shaped catalyst body; and c) calcining the shaped catalyst body to form a catalyst, in which the first metal is supported on a mixed support containing the first zeolite and/or the second zeolite and the binder, wherein the first zeolite has a silica-alumina ratio (SAR) of 5 to 300 and a 10-membered ring pore structure, and the second zeolite has a silica-alumina ratio (SAR) of 5 to 300 and a 12-membered ring pore structure with a pore diameter of 6 to 9 Å, and wherein the first metal is selectively supported on the refractory inorganic oxide binder in the mixed support, the amount of the first metal supported being in the range of 0.01 to 5 wt % on the basis of the weight of the mixed support.

According to an exemplary embodiment, the method may further comprise d) subjecting the catalyst in which the first metal is supported on the mixed support to a reduction treatment or a sulfidation treatment.

According to an exemplary embodiment, step a) may comprise:

contacting a solution containing the precursor of the first metal with the refractory inorganic oxide binder to form a first metal precursor-impregnated refractory inorganic oxide binder; and drying the first metal precursor-impregnated refractory inorganic oxide binder.

According to an exemplary embodiment, the refractory inorganic oxide may be at least one selected from the group consisting of alumina, silica, aluminum phosphate, titania, zirconia, bentonite, kaolin, clinoptilolite, and montmorillonite.

According to an exemplary embodiment, the first zeolite may be at least one selected from the group consisting of ZSM-5, ZSM-11, ZSM-23, ZSM-48, ZSM-57, EU-2, TNU-9, and MCM-22.

According to an exemplary embodiment, the second zeolite may be at least one selected from the group consisting of mordenite (MOR), beta-zeolite, ZSM-12, ZSM-10, and ZSM-18.

According to an exemplary embodiment, the first metal may be at least one selected from the group consisting of Groups 6, 7, 8, 9, and 10 elements on the periodic table.

According to an exemplary embodiment, the first metal may be at least one selected from the group consisting of platinum (Pt), tungsten (W), rhenium (Re), ruthenium (Ru), iridium (Ir), nickel (Ni), palladium (Pd), and molybdenum (Mo).

According to an exemplary embodiment, the first metal may be at least one selected from the group consisting of platinum (Pt), rhenium (Re), and molybdenum (Mo).

According to an exemplary embodiment, the catalyst may further comprise at least one second metal selected from the group consisting of tin (Sn) and lead (Pb), which is selectively supported on the refractory inorganic oxide binder of the mixed support, the amount of the second metal being in the range of 0.01 to 5 wt % on the basis of the weight of the mixed support.

According to an exemplary embodiment, the atomic ratio of the first metal:the second metal may be in the range of 1:0.5 to 50.

In accordance with a second aspect of the present disclosure, there is provided a catalyst for converting aromatic hydrocarbons, which comprises:

(A) a mixed support comprising: (i) a first zeolite, which has a silica-alumina ratio (SAR) of 5 to 300 and a 10-membered ring pore structure, and/or a second zeolite, which has a silica-alumina ratio (SAR) of 5 to 300 and a 12-membered ring pore structure with a pore diameter of 6 to 9 Å; and (ii) a refractory inorganic oxide binder; and (B) a first metal selectively supported on the refractory inorganic oxide binder in the mixed support and having hydrogenation activity, wherein the first metal is at least one selected from the group consisting of platinum (Pt), tungsten (W), rhenium (Re), ruthenium (Ru), iridium (Ir), nickel (Ni), palladium (Pd), and molybdenum (Mo), and wherein the amount of the first metal supported is in the range of 0.01 to 5 wt % on the basis of the weight of the mixed support.

According to an exemplary embodiment, the mixed support may comprise, on the basis of the weight of the mixed support, 5 to 95 wt % of the first zeolite and 95 to 5 wt % of the refractory inorganic oxide binder.

According to an exemplary embodiment, the mixed support may comprise, on the basis of the weight of the mixed support, 5 to 95 wt % of the second zeolite and 95 to 5 wt % of the refractory inorganic oxide binder.

According to an exemplary embodiment, the mixed support may comprise, on the basis of the weight of the mixed support, 5 to 70 wt % of the first zeolite, 10 to 90 wt % of the second zeolite, and 1 to 70 wt % of the refractory inorganic oxide binder.

According to an exemplary embodiment, the first metal may be in a reduced form, a partially oxidized form, or a sulfide form.

In accordance with a third aspect of the present disclosure, there is provided a method for producing C8 aromatics, the method comprising:

providing a feedstock containing benzene, toluene, and/or C9+ aromatics; and forming a reaction product containing an increased amount of C8 aromatic hydrocarbons from the feedstock by at least one of disproportionation, transalkylation, and dealkylation reactions in the presence of the catalyst as defined above, wherein the aromatic loss in the reaction product is 1 mol % or less.

In accordance with a fourth aspect of the present disclosure, there is provided a method for producing para-xylene, the method including:

providing a feedstock containing C8 aromatic hydrocarbons; and forming a C8 aromatic hydrocarbon-containing product having an increased amount of para-xylene by an isomerization of the feedstock in the presence of the catalyst as defined above, wherein the xylene loss through hydrogenation in the C8 aromatic hydrocarbon-containing product is 1 mol % or less.

The catalyst according to embodiments of the present disclosure enables a high yield of mixed xylenes while effectively suppressing aromatic loss compared with the conventional catalysts, in a disproportionation/transalkylation/dealkylation of aromatic hydrocarbons (e.g., alkylaromatic hydrocarbons), and can increase the yield of para-xylene while suppressing xylene loss, in an isomerization of C8 aromatic hydrocarbons. As a result, the catalysts can increase efficiency of subsequent para-xylene separation processes, thereby reducing overall process costs, and thus the catalysts are expected to be extensively commercialized in the future.

DETAILED DESCRIPTION OF THE EXEMPLARY EMBODIMENTS

The present disclosure can be all accomplished by the following description. It is to be understood that the following description illustrates preferable embodiments of the present disclosure, but the present disclosure is not necessarily limited thereto. It is also to be understood that the accompanying drawings are included to provide a further understanding of the present disclosure and are not intended to limit the scope of the present disclosure.

The terms used herein may be defined as follows.

The term "heterogeneous catalyst" may refer to a catalyst that is present in a different phase from a reactant in a catalytic reaction. For example, a heterogeneous catalyst may remain undissolved in a reaction medium. When a heterogeneous catalyst is given, the reaction begins with the diffusion and adsorption of reactants onto the surface of the heterogeneous catalyst. After completion of the reaction, a product needs to be desorbed from the surface of the heterogeneous catalyst.

The term "support" may refer to a material (typically a solid-phase material) with a high specific surface area, to which a catalytically active component is attached, and the support may or may not be involved in a catalytic reaction.

The term "disproportionation reaction" refers to a desymmetrizing reaction of the same molecules in which an alkyl radical is transferred from one molecule to the other to form two different products. For example, disproportionation of toluene may result in producing benzene and xylene.

In a narrow sense, the term "transalkylation" refers to a reaction in which at least one alkyl radical (e.g., methyl, ethyl, propyl, butyl, and so on) is transferred from any organic compound to another.

The term "dealkylation" refers to a reaction in which at least one alkyl radical (e.g., methyl, ethyl, propyl, butyl, and so on.) is eliminated from a hydrocarbon compound (specifically, an aromatic compound).

The term "xylene isomerization" may refer to an isomerization reaction in which C8 aromatic hydrocarbons, more specifically, ortho-xylene and/or meta-xylene is converted into para-xylene.

The term "C9+ aromatic" refers to an aromatic hydrocarbon of C9 or more carbon atoms.

The term "C8 aromatic" may refer to an aromatic hydrocarbon including mixed xylene (ortho-xylene, meta-xylene, and para-xylene) and/or ethyl benzene.

The term "C7-aromatic" refers to an aromatic hydrocarbon of C7 or less carbon atoms.

Alkylaromatic Conversion Catalyst

A catalyst according to an embodiment is a heterogeneous catalyst, and may be applied to the selective conversion of a feedstock containing compounds (specifically, benzene, toluene and/or C9+ aromatics (alkylaromatics)) into C8 aromatic compounds (specifically mixed xylenes) by a disproportionation/transalkylation/dealkylation or the selective conversion of C8 aromatic compounds (specifically mixed xylenes, more specifically, ortho-xylene and/or meta-xylene) into a particular isomer, e.g., para-xylene.

In the present embodiment, an aromatic conversion catalyst may be in a form in which a metal having hydrogenation activity (a first metal) is selectively supported on a refractory inorganic oxide binder in a mixed support which comprises a zeolite component containing at least one type of zeolite and a refractory inorganic oxide binder. The zeolite which is combined with the inorganic oxide binder to constitute the mixed support may comprise: (i) a first zeolite having a 10-membered ring pore structure; and/or (ii) a second zeolite having a 12-membered ring pore structure with a particular pore diameter (specifically, in the range of 6 to 9 Å).

Mixed Support

First Zeolite

In an embodiment, the zeolite having a 10-membered ring pore structure, as a first zeolite component, may be at least one selected from the group consisting of ZSM-5, ZSM-11, ZSM-23, ZSM-48, ZSM-57, EU-2, TNU-9, and MCM-22. According to an exemplary embodiment, ZSM-5 may be representatively used as the first zeolite. ZSM-5, which is a synthetic zeolite having an MFI framework, has a chemical formula per unit cell expressed by $(H,Na)_n[Al_nSi_{96-n}O_{192}]$, a pore diameter (size) of less than about 6 Å, specifically 0.51×0.55 nm (5.1×5.5 Å) for straight channels and 0.53×0.56 nm (5.3×5.6 Å) for zigzag channels. The details of the first zeolite are described in Atlas of Zeolite Framework Types, 5th Revised Edition, Elsevier (2001), which is incorporated by reference herein. In addition, the first zeolite may be in an ammonium form or a hydrogen form.

The silica-alumina ratio (SAR) of the first zeolite may affect catalytic activity (especially, acid characteristics), and it may be advantageous to use a zeolite type, the SAR of which is adjusted to a range suitable for suppressing the occurrence of side reactions and improving the yield of C8 aromatics (especially, mixed xylenes) from alkylaromatics (for example, benzene, toluene and/or C9+ aromatics) or the yield of para-xylene from C8 aromatics (for example, para-xylene-deficient mixed xylenes). The SAR of the first zeolite may be in the range of, for example, about 5 to 300, specifically, about 10 to 250, and more specifically about 20 to 200.

Second Zeolite

According to an embodiment, a zeolite type having a 12-membered ring pore structure with a pore diameter in the range of about 6 to 9 Å may be used as a second zeolite component. In an exemplary embodiment, the SAR of the second zeolite may be in the range of, for example, about 5 to 300, specifically, about 10 to 250, and more specifically about 15 to 200. At least one selected from the group consisting of mordenite (MOR), beta-zeolite, ZSM-12, ZSM-10, and ZSM-18 may be used as a second zeolite having the above-described pore properties. According to a particular embodiment, mordenite and beta-zeolite may be exemplified as the second zeolite, and these may be used alone or in combination. In addition, the second zeolite may be in an ammonium form or a hydrogen form.

The details of the second zeolite are described in Atlas of Zeolite Framework Types, 5th Revised Edition, Elsevier (2001), which is incorporated by reference herein.

Refractory Inorganic Oxide Binder

According to an embodiment, the hydrogenation metal (a first metal) of the catalyst is selectively supported on a refractory inorganic oxide binder, which is one of the components constituting the mixed support. In general, a binder can facilitate the preparation of the catalyst, and provides sufficient strength to the catalyst, and is also used for the purpose of binding zeolite components so as to facilitate the binding, dispersion, or close intermixing of the zeolite components. However, in the present embodiment, it should be noted that the binder provides a site on which the active metal is supported, without limitation to the typical functions of a binder.

While the present disclosure is not bound by a particular theory, it is considered that the hydrogenation metal is supported on only the inorganic oxide binder, but not on the zeolite component (that is, first and/or second zeolite), in the mixed support, thereby achieving the effects of increasing reaction activity and controlling excessive hydrogenation. Consequently, in a disproportionation/transalkylation/dealkylation of alkylaromatics, the increase of reaction activity allows the reaction to be carried out at a relatively low temperature, thereby reducing variable costs, and the suppression of excessive hydrogenation allows the aromatic loss to be reduced, thereby increasing xylene yields and reducing hydrogen consumption. Furthermore, in the isomerization of xylenes, the increase of reaction activity allows the reaction to be carried out at a relatively low temperature, thereby reducing variable costs, and the suppression or control of excessive hydrogenation can increase para-xylene yields and reducing hydrogen consumption.

According to an exemplary embodiment, the inorganic oxide binder may be selected from the types of inorganic oxides that have a comparatively larger specific surface area. According to an exemplary embodiment, the inorganic oxide binder may have a specific surface area (BET) of for example, about 20 to 1000 $m^2/g$, specifically, about 30 to 700 $m^2/g$, and more specifically about 50 to 500 $m^2/g$.

In an exemplary embodiment, the inorganic oxide binder may be, for example, at least one selected from the group consisting of alumina, silica, aluminum, phosphate, titania, zirconia, bentonite, kaolin, clinoptilolite, and montmorillonite. According to a particular embodiment, the inorganic binder may be amorphous, and thus, specifically, at least one selected from the group consisting of alumina, silica, and aluminum phosphate, and more specifically, gamma-alumina and/or silica may be used.

In an exemplary embodiment, the mixed support may comprise the first zeolite and the inorganic oxide binder, wherein, on the basis of the weight of the mixed support, the content of the first zeolite may be in the range of for example about 5 to 95 wt %, specifically about 10 to 90 wt %, and more specifically about 30 to 80 wt %, and the content of the refractory inorganic oxide binder may be in the range of for example about 95 to 5 wt %, specifically about 90 to 10 wt %, and more specifically about 70 to 20 wt %.

In another exemplary embodiment, the mixed support may comprises the second zeolite and the inorganic oxide binder, wherein, on the basis of the weight of the mixed support, the content of the second zeolite may be in the range of for example about 5 to 95 wt %, specifically about 10 to 90 wt %, and more specifically about 30 to 80 wt %, and the content of the refractory inorganic oxide binder may be in the range of for example about 95 to 5 wt %, specifically about 90 to 10 wt %, and more specifically about 70 to 20 wt %.

In still another exemplary embodiment, the composition of the mixed support may include, on the basis of the weight of the mixed support, (i) the first zeolite of about 5 to 70 wt % (specifically, about 10 to 60 wt %, more specifically about 15 to wt %), (ii) the second zeolite of about 10 to 90 wt % (specifically, about 20 to 80 wt %, more specifically, about 30 to 70 wt %), and (iii) the inorganic binder of about 1 to 70 wt % (specifically, about 5 to 60 wt %, and more specifically about 10 to 50 wt %). The mixing ratio of the first zeolite:the second zeolite (on the basis of the weight of zeolite) can be controlled in the range of for example, 1:about 0.2 to 9, specifically, 1:about 0.5 to 8, and more specifically, 1:about 2 to 6. In cases where a combination of two types of zeolites is used as such, the first zeolite serves a function of dealkylation, isomerization, or the like and the second zeolite serves a function of transalkylation, disproportionation, dealkylation, isomerization, or the like, and thus it may be advantageous to control the mixing ratio of the first and second zeolites to the above-described range for an appropriate balance therebetween.

According to an exemplary embodiment, the mixed support may have an apparent packing density in the range of about 0.3 to 1.5 cc/g, specifically about 0.5 to 1.0 cc/g, and more specifically about 0.6 to 0.8 cc/g. Meanwhile, the pore volume of the mixed support may be in the range of for example about 0.1 to 1 cc/g, specifically about 0.15 to 0.9 cc/g, and more specifically about 0.2 to 0.8 cc/g. Besides, the specific surface area (BET) of the mixed support may be in the range of for example about 100 to 800 $m^2/g$, specifically about 200 to 700 $m^2/g$, and more specifically about 300 to 600 $m^2/g$. The numerical ranges of the above-described physical properties can be understood as exemplary.

According to an exemplary embodiment, the mixed support of the catalyst may be in a cylindrical shape, and may have, for example, a diameter of about 0.5 to 5 mm (specifically about 1 to 3 mm) and a length of about 2 to 20 mm (specifically about 3 to 15 mm). The mixed support may have a shape of granule, pellet, tablet, sphere, trilobite, clover, honeycomb, or the like, in addition to the cylindrical shape.

First Metal (Hydrogenation Metal)

In a bifunctional catalyst according to an embodiment, a first metal selectively supported on the inorganic oxide binder in the mixed support is a metal with hydrogenation activity known in the art. For example, at least one selected from the group consisting of Groups 6, 7, 8, 9, and 10 on the periodic table may be used as the first metal. According to an exemplary embodiment, the first metal may be at least one selected from the group consisting of platinum (Pt), tungsten (W), rhenium (Re), ruthenium (Ru), iridium (Ir), nickel (Ni), palladium (Pd), and molybdenum (Mo). In a particular embodiment, the first metal may be at least one selected from the group consisting of platinum (Pt), rhenium (Re), and molybdenum (Mo).

According to an embodiment, the amount of the first metal may be in the range of about 0.01 to 5 wt %, specifically about 0.012 to 3.5 wt %, and more specifically about 0.015 to 2.5 wt %, on the basis of the weight of the mixed support.

Meanwhile, the first metal may be in a reduced form, a partially oxidized form (for example, a partially oxidized form of $Mo_{4+}$ but not $Mo_{6+}$ when the first metal is molybdenum (Mo)), or a sulfide form.

In a particular embodiment, the first metal may be platinum. However, in its reduced form, strong hydrogenation activity may cause the loss of an aromatic ring. Therefore, when such a first metal is converted into a sulfide form, the hydrogenation activity is reduced to a proper level, thereby additionally suppressing the loss resulting from aromatic hydrogenation.

In another particular embodiment, the first metal may be rhenium, wherein rhenium may be in a reduced form or a sulfide form. When, similar to platinum, rhenium in a reduced form causes side reactions due to excessive hydrogenation functions, rhenium may be introduced in a sulfide form.

In another particular embodiment, the first metal may be molybdenum, wherein molybdenum may be in the form of $MoO_2$ obtained by a partial reduction of $MoO_3$ (that is, a partially oxidized form) or a sulfide (that is, $MoS_2$). The reason is that molybdenum has low hydrogenation activity when having an oxidation value of 6+, but can provide a hydrogenation function when being in the form of an oxide or sulfide having an oxidation value of 4+.

Second Metal (Optional Component for Controlling Hydrogenation Activity of First Metal)

According to an exemplary embodiment, when the hydrogenation activity of the first metal is excessively high (for example, excessive hydrogenation activity is exhibited when only the first metal is supported), the second metal may be introduced together with the first metal for controlling the hydrogenation activity of the first metal, and can be selectively supported on the inorganic oxide of the mixed support as well. Specifically, since platinum has high hydrogenation activity, it may be advantageous to suppress the generation of naphthene, caused by the hydrogenation of an aromatic ring, by introducing the second metal, together with platinum, to the catalyst for the purpose of controlling the hydrogenation activity of platinum as needed. The second metal may be at least one selected from the group consisting of tin (Sn) and lead (Pb).

According to an exemplary embodiment, the second metal may be introduced in an amount in the range of about 0.01 to 5 wt %, specifically about 0.1 to 3 wt %, and more specifically about 0.2 to 1 wt %, on the basis of the weight of the mixed support. The atomic ratio of the first metal:the second metal may be controlled within the range of, for example, 1:about 0.5 to 50, specifically, 1:about 5 to 40, and more specifically, 1:about 10 to 20.

In a particular embodiment, when platinum is used as the first metal, the second metal may be used in combination with platinum. When the relative amount of the second metal supported is excessively low or high, side reactions due to excessive hydrogenation activity of platinum (especially, a reduced form of platinum) is caused or a suitable hydrogenation function is not exhibited, and rather, the yield of mixed xylenes may be lowered and cokes may be formed, and thus it may be advantageous to control the amount of the second metal supported within the above-described ranges as appropriate. However, these ranges can be understood as exemplary.

According to an exemplary embodiment, the first and second metals may be present in an alloy form on the mixed support, and alternatively may be present in the form of being dispersed or distributed spaced apart from each other. Even when the first and second metals are spaced apart from each other, it may be advantageous that the first and second metals are adjacent to each other if possible to thereby electrically and/or chemically affect each other.

Method for Preparing Catalyst

A method for preparing a catalyst for an aromatic conversion reaction (a disproportionation/transalkylation/dealkylation of alkylaromatics or an isomerization of xylenes) according to an embodiment is as follows.

Preparation of First Metal Precursor-Supported (or First and Second Metal Precursors-Supported) Refractory Inorganic Oxide Binder First, a step of supporting a first metal (or first and second metals) having hydrogenation activity on a refractory inorganic oxide binder may be performed.

As described above, the inorganic oxide binder may be, for example, at least one selected from the group consisting of alumina, silica, aluminum, phosphate, titania, zirconia, bentonite, kaolin, clinoptilolite, and montmorillonite. According to a particular embodiment, the inorganic oxide binder may be alumina, for example, gamma-alumina. Since gamma-alumina may be derived from boehmite or pseudo-boehmite alumina, such an alumina precursor may be used in the supporting of a metal component.

In an exemplary embodiment, for the introduction of the first metal into the inorganic oxide binder, a supporting or incorporation method known in the art, such as a manner using a metal precursor, for example, co-precipitation or impregnation (for example, initial wet impregnation, excess solution impregnation, and immersion) may be applied.

According to a particular embodiment, the first metal (or the first and second metals) may be introduced onto the mixed support in an impregnation manner using a metal precursor (typically a water-soluble or solvent-soluble metal compound).

When the first metal is platinum, at least one selected from hydrides, fluorides (e.g., $PtF_6$, $PtF_4$, $[PtF_5]_4$, etc), chlorides (e.g., $H_2PtCl_6$, $PtCl_3$, $PtCl_4$, $Pt_6Cl_{12}$, etc), bromides (e.g., $PtBr_3$, $PtBr_4$, etc), iodides (e.g., $PtI_2$, $PtI_3$, $PtI_4$, etc), oxides (e.g., PtO, $PtO_2$, PtO, etc), sulfides (e.g., PtS, $PtS_2$, etc), carbonyls (e.g., $Pt(CO)_4$) and/or complexes (e.g., $[PtCl_2(NH_3)_2]$, $[PtCl_2(NH_3)_2]$, $K_2[PtCl_6]$, $K_2[Pt(CN)_4]$, $PtCl_4.5H_2O$, $K[PtCl_3(NH_3)]$, $Na_2[PtBr_6].6H_2O$, $(NH_4)_2[PtBr_6]$, $K_2[PtI_6]$, $(NH_4)_2[PtCl_6]$, $K_2[Pt(CN)_6]$, $(NH_4)_2[PtCl_4]$, $K_2[Pt(NO_2)_4]$, $K[PtCl_3(C_2H_4)].H_2O$ $[Pt(NH_3)_4](NO_3)_2$, $H_2PtCl_6$, etc) may be used as a platinum precursor, but is not limited thereto.

For a molybdenum precursor, at least one selected from molybdenum(II) acetate, ammonium(VI) molybdate, diammonium(III) dimolybdate, ammonium(VI) heptamolybdate, ammonium(VI) phospho molybdate and similar sodium and potassium salts, molybdenum (III) bromide, molybdenum (III)-(V) chloride, molybdenum(VI) fluoride, molybdenum (VI) oxychloride, molybdenum(IV)-(VI) sulfide, molybdic acid and corresponding acid ammoniums, sodium and potassium salts, molybdenum (II-VI) oxide, and the like may be used, but is not limited thereto.

For a rhenium precursor, at least one selected from perrhenic acid, ammonium perrhenate, rhenium oxide complexes, $ReO_2$, $ReO_3$, $Re_2O_7$, and the like may be used, but is not limited thereto.

Meanwhile, the second metal introduced to control the hydrogenation activity of the first metal may be introduced together with the first metal or may be introduced into the inorganic oxide binder sequentially (before or after supporting the first metal).

According to an exemplary embodiment, a tin precursor in the second metal may be at least one selected from tin chloride, tin bromide, tin iodide, tetramethoxy tin, tetraethoxy tin, tetrabutoxy tin, tetraphenoxy tin, tin sulfide, tin oxide, tin sulfate, tin nitrate, tin selenide, tin peroxide, $Na_2SnO_3$, $Na_2SnO_3.3H_2O$, $Sn(OH)_2$, tin nitride, tin acetate, tin oxalate, and the like. In addition, a lead precursor may be at least one selected from lead nitrate, lead chloride, lead carbonate, $Pb(acac)_2$, lead acetate, and the like.

According to an exemplary embodiment, the concentration of the first metal and/or the second metal in the precursor solution for impregnation or the like may be in the range of for example about 0.005 to 1 M, specifically about 0.01 to 0.5 M, and more specifically about 0.015 to 0.3 M. The conditions for impregnation are not particularly limited, but for example, impregnation may be performed at about 1 to 100° C. (specifically about 25 to 60° C.) for about 0.1 to 48 hours (about 0.5 to 12 hours), but these conditions may be understood as exemplary. The inorganic oxide binder on which the first metal precursor (or the first and second metal precursors) is supported can be obtained through the above-described impregnation procedure.

As described above, the metal is impregnated on the inorganic oxide binder, followed by drying, and for example, the drying step may be performed in an oxygen-containing atmosphere (specifically air), and the drying temperature may be in the range of for example about 60 to 200° C., and specifically about 80 to 150° C. In addition, the drying time may be determined in the range of for example about 0.5 to 15 hours, and specifically about 1 to 12 hours. The metal precursor may be closely attached to the inorganic oxide binder through the drying step.

Preparation of Shaped Catalyst Body (or Catalyst Body)

According to an embodiment, a step of combining a zeolite component (that is, a first zeolite and/or a second zeolite) with the previously prepared first metal precursor-supported (first and second metals-supported) binder, followed by shaping, thereby preparing a shaped catalyst body may be performed.

According to an exemplary embodiment, the zeolite component may be in an ammonium form. Alternatively, the ammonium form of zeolite may be converted into a hydrogen form of zeolite by thermal treatment, such as calcining. The reason why the zeolite component is converted into an ammonium form or a hydrogen form is that acid (solid acid) catalyst activity is difficult to secure in a sodium form.

Furthermore, it may be advantageous to convert the zeolite component into a hydrogen form through a pretreatment during the catalyst preparation or before reactions.

According to an exemplary embodiment, when two types of zeolites are both used, the first metal precursor-containing (or first and second metal precursors-containing) binder may be first combined with any one type of zeolite, and then may be sequentially combined with the other type of zeolite. Alternatively, the first metal precursor-containing (or first and second metal precursors-containing) binder may be simultaneously combined with two types of zeolites. In still another embodiment, the first zeolite and the second zeolite are first combined with each other, and then may be combined with the first metal precursor-containing (or first and second metal precursors-containing) binder.

According to an exemplary embodiment, extrusion, spray drying, pelletizing, oil dropping, and the like may be exemplified as a method of combining and shaping the zeolite component and the first metal precursor-containing (or first and second metal precursors-containing) binder.

After the catalyst body is formed as described above, any conventional post-treatment, for example, washing with water may be performed.

A drying step may be performed, as a subsequent step, in an oxygen-containing atmosphere (specifically air), and the drying temperature may be in the range of for example about 60 to 200° C., and specifically about 80 to 150° C. In addition, the drying time may be determined in the range of for example about 0.5 to 15 hours, and specifically about 1 to 12 hours.

Then, a calcination (or heat-treatment) step for the dried catalyst body may be performed in an oxygen-containing atmosphere (for example air) or an inert gas (for example, nitrogen or the like) atmosphere under a temperature condition of about 300 to 800° C., and specifically about 400 to 650° C. In addition, the calcination time may be controlled in the range of for example about 0.5 to 24 hours, and specifically about 1 to 12 hours.

Reduction Step

According to an embodiment, a step of subjecting the calcined catalyst body to a reduction treatment may be performed. In the reduction treatment step, hydrogen may be used alone, or may be diluted with an inert gas (for example, $N_2$, He, Ar, or the like) for use. For example, the reduction treatment may be performed at a temperature of about 25 to 800° C., specifically about 200 to 700° C., and more specifically about 300 to 550° C., and the reduction treatment time may be controlled in the range of for example, about 0.5 to 24 hours, and specifically about 1 to 12 hours, but is not particularly limited thereto.

The metal (the first metal, or the first and second metals) distributed on the inorganic oxide binder in the mixed support may be converted into a reduced form through the reduction treatment.

Through the above-described procedure, an oxide of the first metal (or oxides of the first and second metals) may be present in a reduced form or a partially reduced (or partially oxidized) form. By way of example, the metal contained in the catalyst may have, for example, an element form, by a reduction treatment, and may be used as a catalyst for a disproportionation/transalkylation/dealkylation or a xylene isomerization to be described later.

Sulfidation Step

In order to control excessive hydrogenation activity (especially for platinum and rhenium) to induce side reactions, such as aromatic loss, by the first metal, or in order to impart a hydrogenation function (especially for molybdenum), the conversion into a sulfide form rather than a reduced form may be performed as an optional step. According to an exemplary embodiment, the reduced catalyst body may be subjected to a sulfidation treatment, and as a result, the first metal (or the first and second metals) may be present in a sulfide form.

Since a metal component in a catalyst body can be converted into a sulfide by a method known in the art, such sulfidation can be applied in a gas-phase (contacting with hydrogen sulfide or a mixture of hydrogen sulfide and an inert gas) or a liquid-phase (contacting with a sulfur compound-containing solution). According to a particular embodiment, the reduced catalyst body may be treated with a solution containing a sulfur compound.

According to an exemplary embodiment, a sulfur compound that can be used in the sulfidation may be at least one selected from hydrogen sulfide, hydrogen disulfide, carbon disulfide, alkyl sulfide, and the like. Specifically, examples of the alkyl sulfide may include methyl sulfide, dimethyl sulfide, dimethyl disulfide, diethyl sulfide, and/or dibutyl sulfide. In addition, a hydrocarbon-based solvent, such as benzene, toluene, xylene, C9+ aromatics, hexane, or heptane, may be used as a solvent in the sulfidation. As an example, the amount of a sulfur compound in the solution for the sulfidation may be appropriately determined to be an equivalent weight required to sulfide the metal in the catalyst body or higher. For example, when molybdenum is used as the first metal, a sulfur compound having an equivalent required to sulfide molybdenum to $MoS_3$, which may be finally converted into $MoS_2$, or higher may be mixed in a solution for use.

In an exemplary embodiment, the sulfidation may be performed at a temperature of room temperature to 500° C. (specifically about 100 to 450° C.) for about 0.5 to 100 hours (specifically about 1 to 48 hours).

Disproportionation/Transalkylation/Dealkylation Reaction

In an embodiment, a process is provided wherein a feedstock containing aromatics, especially, alkylaromatics is converted into C8 aromatic hydrocarbons by a reaction using the above-described catalyst.

The alkylaromatic hydrocarbon is a compound in which at least one alkyl group is attached to an aromatic ring, and examples of the alkyl group may be a methyl group, an ethyl group, a propyl group, a butyl group, and the like, and specifically, toluene, ethyl toluene, propyl benzene, tetramethyl benzene, ethyldimethyl benzene, diethyl benzene, methylpropyl benzene, ethylpropyl benzene, triethyl benzene, diisopropylbenzene, and a mixture thereof.

In addition, the feedstock may further contain not only the above-described alkylaromatic hydrocarbons but also an aromatic compound without an alkyl group attached thereto, such as benzene. In an exemplary embodiment, the feedstock may contain benzene, toluene, and/or C9+ aromatics. However, it is not excluded that C8+ aromatics (e.g., ortho-xylene, meta-xylene, para-xylene, ethyl benzene, or the like) are contained in the feedstock. Therefore, the feedstock may contain toluene or C9+ aromatic compounds (specifically, C9 and/or C10 aromatic compounds) alone, contain a mixture in which toluene and C9+ aromatics are combined at any ratios, or contain benzene, toluene, and C9+ aromatics.

According to an exemplary embodiment, the feedstock containing alkylaromatics may be derived from: a catalytic reforming reaction of naphtha; a pyrolytic reaction of naphtha, distillates, or other hydrocarbons that produce light olefins and aromatic-rich fractions; a catalytic cracking or pyrolytic reaction of heavy fractions that produce gasoline boiling range hydrocarbons; or the like, and such sources may be used alone or in combination as a feedstock. Optionally, such reactant sources may be subjected to any pre-treatment steps known in the art, including hydrotreatment, prior to the reaction, for the purpose of eliminating impurities (e.g., components that can affect catalytic activity and product distribution, such as sulfur or olefins).

According to an embodiment, a feedstock containing alkylaromatics may be subjected to at least one of disproportionation, transalkylation, and dealkylation reactions under predetermined reaction conditions. For example, there are a disproportionation reaction of toluene, a transalkylation reaction of toluene/C9 aromatic compounds, a dealkylation reaction of alkylaromatic compounds, and the like, and, as a result, C8 aromatic compounds may be produced through the above-described reactions.

According to an exemplary embodiment, the above-described reactions may be performed in a gas phase or a liquid phase with supply of hydrogen, wherein the molar ratio of hydrogen/hydrocarbon may be controlled in the range of for example about 0.1 to 20, specifically about 0.5 to 7, and more specifically about 1 to 5. In addition, as for a reactor, a reactor form known in the art, for example, a fixed bed reactor, a batch reactor, a semi-batch reactor, a fluidized bed reactor, a slurry reactor, or the like may be used.

Meanwhile, the above-described reaction may be performed under conditions of for example, a temperature of about 200 to 600° C. (specifically about 250 to 550° C. and more specifically about 300 to 500° C.) and a pressure of about 5 to 100 $kgf/cm^2$ (specifically about 10 to 80 $kgf/cm^2$, and more specifically about 20 to 60 $kgf/cm^2$). The above-described reaction conditions can be understood as exemplary, and thus can be changed depending on the composition of the feedstock, or the like.

According to another embodiment, the reaction may be performed in a continuous mode, wherein the weight hourly space velocity (WHSV) may be controlled within the range of for example about 0.1 to 20 $hr^1$, specifically about 1 to 10 $hr^{-1}$, and more specifically about 2 to 5 $hr^{-1}$, but these can be understood as exemplary.

According to the present embodiment, the alkylaromatic-containing feedstock is converted into C8 aromatics (mainly mixed xylenes) by disproportionation/transalkylation/dealkylation, and it is notable to maintain favorable C8 aromatic yields and significantly low aromatic loss, especially compared with a case where the conventional zeolite-based transalkylation catalyst is used.

The aromatic loss in the disproportionation/transalkylation/dealkylation may be for example about 1 mol % or less, specifically about 0.7 mol % or less, and more specifically about 0.5 mol % or less.

Xylene Isomerization Reaction

According to an embodiment, a process is provided wherein a feedstock containing C8 aromatics, specifically mixed xylenes (a mixture of ortho-xylene, meta-xylene, and para-xylene), more specifically a non-equilibrium of mixed xylenes (a xylene mixture where an isomer of at least one type of C8 aromatic compound is present at a concentration lower than equilibrium, for example, para-xylene has a low concentration compared with an equilibrium state) is converted into a thermodynamic equilibrium of xylene by a reaction using the above-describe catalyst.

The feedstock of the xylene isomerization may be a C8 hydrocarbon fraction produced from a refining process, e.g., a C8 aromatic hydrocarbon fraction that is separated and recovered by selective fractionation or distillation of catalytically cracked or reformed hydrocarbons. In a particular embodiment, the C8 aromatic hydrocarbon fraction may be a C8 aromatic fraction obtained by the disproportionation/transalkylation/dealkylation of the above-described alkylaromatic hydrocarbon fraction.

According to an alternative embodiment, the feedstock of the xylene isomerization is a residual fraction after the separation of a particular C8 aromatic isomer, such as para-xylene, from a xylene isomerization reaction product, or may be a combination of such a residual fraction and a new feedstock for the xylene isomerization.

According to an exemplary embodiment, the feedstock of the xylene isomerization may contain ortho-xylene of about 100 wt % or less (specifically about 20 to 80 wt %, and more specifically about 30 to 70 wt %), meta-xylene of about 100 wt % or less (specifically about 20 to 80 wt %, and more specifically about 30 to 70 wt %), and para-xylene of about 30 wt % or less (specifically about 20 wt % or less, and more specifically about 10 wt % or less). In addition, para-xylene may be separated and recovered from the feedstock by a method known in the art prior to the isomerization.

In addition, the feedstock of the xylene isomerization may further contain ethyl benzene. The content of ethyl benzene in the feedstock may be in the range of for example about 90 wt % or less (specifically about 50 wt % or less, and more specifically about 20 wt % or less).

In an exemplary embodiment, the xylene isomerization temperature may be controlled in the range of for example about 150 to 700° C., specifically about 250 to 600° C., and more specifically about 300 to 500° C. In addition, the xylene isomerization may be performed with supply of hydrogen, and the reaction pressure may be controlled in the range of for example about 1 to 100 $kgf/cm^2$, specifically about 3 to 80 $kgf/cm^2$, and more specifically about 5 to 60 $kgf/cm^2$. In an exemplary embodiment, any diluent gas component (specifically, an inert diluent gas component) such as nitrogen, argon, and/or light hydrocarbons together with hydrogen may be supplied.

Besides, the xylene isomerization may be performed in a gas phase, a gas-liquid mixed phase, or a liquid phase, wherein the molar ratio of hydrogen/hydrocarbon may be controlled in the range of for example about 0.1 to 20, specifically about 0.5 to 7, and more specifically about 0.7 to 5.

Meanwhile, the isomerization may be performed using a fixed bed reactor, a moving bed reactor, a fluidized bed reactor, a slurry reactor or ebullated bed reactor, a bath reactor, or the like. According to a particular embodiment, the isomerization may be performed in a continuous mode, wherein the weight hourly space velocity (WHSV) may be controlled within the range of for example about 0.3 to 50 $hr^{-1}$, specifically about 0.5 to 30 $hr^{-1}$, and more specifically about 1 to 20 $hr^{-1}$, but these can be understood as exemplary.

As such, the product may have a reduced ethyl benzene content and an ortho- and/or meta-xylene contents but an increased para-xylene content compared with the feedstock.

As an example, when the feedstock contains ethyl benzene, the conversion of such ethyl benzene may be for example at least about 50%, specifically at least about 70%, and more specifically at least about 75%. In addition, the amount of xylene lost in the middle of hydrogenation during the isomerization may be about 1 wt % or less, specifically about 0.7 wt % or less, and more specifically about 0.5 wt % or less.

From the above-described xylene isomerization products, a particular xylene isomer, especially para-xylene is separated and recovered, and the non-recovered fraction may be recycled as a feedstock, or combined with another fraction (specifically, a new feedstock of the xylene isomerization) and then again introduced to a reaction zone.

The present disclosure can be more clearly understood by the following examples, and these examples are merely illustrative of the present disclosure and are not intended to limit the scope of the disclosure.

EXAMPLES

The materials used in the present examples and comparative examples are as follows.

Metal compounds were ACS Reagent Grade products purchased from Sigma-Aldrich and zeolites were purchased from Zeolyst. In addition, for a disproportionation/transalkylation/dealkylation and a xylene isomerization, raw materials were purchased in commercial processes.

Comparative Example 1

Molybdenum (Mo) Impregnation after Preparation of Extruded Mixed Support (ZSM-5/MOR/Alumina)

A hydrogen form of mordenite having a silica/alumina molar ratio (SAR) of 20 and a hydrogen form of ZSM-5 having a silica/alumina molar ratio (SAR) of 30 were extruded into a cylinder shape with a diameter of 1.6 mm and a length of 3 mm by using pseudoboehmite, which is a precursor of gamma-alumina, as an inorganic binder. Herein, the catalyst extrudate contained 60 wt % of mordenite and 25 wt % of ZSM-5. The catalyst extrudate as a mixed support was dried at 150° C. for 10 hours, and subsequently fired at 500° C. for 3 hours.

Then, an aqueous solution of ammonium heptamolybdate (0.06 M) was impregnated onto the mixed support such that 2.0 parts by weight of molybdenum was contained in 100 parts by weight of the mixed support, followed by drying at 150° C. for 10 hours and then calcining at 500° C. for 3 hours, to prepare a catalyst body.

A fixed bed continuous reactor was charged with 2.0 g of the catalyst body thus prepared, and the atmosphere in the reactor was replaced with nitrogen, and then the pressure in the reactor was raised to 30 kg/cm$^2$. Thereafter, nitrogen was replaced with hydrogen, and the temperature was raised to 230° C. while 82 cc/min of hydrogen was allowed to flow, and then the temperature was maintained for 5 hours while 0.15 cc/min of toluene mixed with 2.0 wt % of DMDS was allowed to flow, and the temperature was raised to 350° C., followed by a sulfidation treatment for 6 hours.

Thereafter, a feedstock composed of 50 wt % of a C7-aromatic fraction containing toluene as a main component and 50 wt % of a C9+ aromatic fraction containing C9 aromatics as a main component was introduced. While 0.135 cc/m of the feedstock was allowed to flow, a disproportionation/transalkylation reaction was performed. The results are shown in Table 1.

Comparative Example 2

Co-Mulling of Molybdenum (Mo) and Mixed Support

In the extrusion process of a hydrogen form of mordenite having a silica/alumina molar ratio (SAR) of 20 and a hydrogen form of ZSM-5 having a silica/alumina molar ratio (SAR) of 30 by using pseudoboehmite as an inorganic binder, an aqueous solution of ammonium heptamolybdate (0.06 M) was mixed therewith such that the percentages of mordenite and ZSM-5 in the mixed support, excluding molybdenum, were controlled to 60 wt % and 25 wt %, respectively. In addition, the amount of molybdenum supported was controlled to be 2.0 parts by weight on the basis of the total of 100 parts by weight of the mordenite/ZSM-5/inorganic binder (mixed support). The catalyst extrudate was prepared as a cylindrical shape with a diameter of 1.6 mm and a length of 3 mm. After the shaping, the catalyst extrudate was dried at 150° C. for 10 hours, and subsequently fired at 500° C. for 3 hours, thereby preparing a catalyst body.

A sulfidation treatment was carried out by the same method as in Comparative Example 1, and the results are shown in Table 1 below.

Comparative Example 3

Selective Supporting of Molybdenum (Mo) on Zeolite (MOR/ZSM-5)

A hydrogen form of mordenite having a silica/alumina molar ratio (SAR) of 20 and a hydrogen form of ZSM-5 having a silica/alumina molar ratio (SAR) of 30 were first mixed. Thereafter, an aqueous solution of ammonium heptamolybdate (0.07 M) was impregnated onto the mixed zeolite, followed by drying at 150° C. for 10 hours, subsequently calcining at 500° C. for 3 hours.

The molybdenum-supported zeolite thus prepared was mixed with pseudoboehmite to prepare a cylindrical shape with a diameter of 1.6 mm and a length of 3 mm. After the shaping, the catalyst extrudate was dried at 150° C. for 10 hours, and subsequently fired at 500° C. for 3 hours, thereby preparing a catalyst body.

In the catalyst body thus prepared, the percentages of mordenite and ZSM-5 in the mixed support, excluding molybdenum, were controlled to 60 wt % and 25 wt %, respectively. The amount of molybdenum supported was controlled to be 2.0 parts by weight on the basis of the total of 100 parts by weight of the mordenite/ZSM-5/inorganic binder (mixed support).

A sulfidation treatment was carried out by the same method as in Comparative Example 1, and the results are shown in Table 1 below.

Example 1

Selective Supporting of Molybdenum (Mo) on Binder

An aqueous solution of ammonium heptamolybdate (0.5 M) was first impregnated onto pseudoboehmite as an inorganic binder, followed by drying at 120° C. for 2 hours, and then mixed with a hydrogen form of mordenite having a silica/alumina molar ratio (SAR) of 20 and a hydrogen form of ZSM-5 having a silica/alumina molar ratio (SAR) of 30 to prepare a catalyst extrudate having a cylindrical shape with a diameter of 1.6 mm and a length of 3 mm. The catalyst extrudate was dried at 150° C. for 10 hours, and subsequently fired at 500° C. for 3 hours, thereby preparing a catalyst body.

In the catalyst body thus prepared, the percentages of mordenite and ZSM-5 in the mixed support, excluding molybdenum, were controlled to 60 wt % and 25 wt %, respectively. The amount of molybdenum supported was controlled to be 2.0 parts by weight on the basis of the total of 100 parts by weight of the mordenite/ZSM-5/inorganic binder (mixed support).

A sulfidation treatment was carried out by the same method as in Comparative Example 1, and the results are shown in Table 1 below.

The conversion, xylene yield, and aromatic loss were calculated by Equations 1 to 3 below, respectively.

Conversion (%)=[1−(content of toluene in produced fraction+$C9A$, wt %)/(content of toluene in fed fraction+$C9A$, wt %)]*100 [Equation 1]

Xylene yield (wt %)=content of xylene in produced fraction, wt % [Equation 2]

Aromatic loss (mol %)=[1−(aromatic in produced fraction, mol %)/(aromatic in fed fraction, mol %)]*100 [Equation 3]

TABLE 1

| | Comparative Example 1 | Comparative Example 2 | Comparative Example 3 | Example 1 |
|---|---|---|---|---|
| Mo supporting | Supporting after mixed support shaping | Co-mulling | Selective supporting on zeolite | Selective supporting on binder |
| Reaction temperature (° C.) | 343 | 345 | 349 | 332 |
| Conversion (%) | 45.0 | 44.6 | 44.7 | 45.1 |
| Xylene yield (wt %) | 34.12 | 34.16 | 34.01 | 35.10 |
| Aromatic loss (mol %) | 1.09 | 1.10 | 1.19 | 0.43 |

According to the above table, compared with Comparative Examples 1 to 3, Example 1 showed a similar conversion even at the lowest reaction temperature, and as for the xylene yield, the catalyst in which the molybdenum (Mo) metal was supported on only the binder (Example 1) was also most excellent. It was specifically verified that the use of the catalyst according to Example 1 showed a decrease in aromatic loss at a significantly low level compared with the comparative examples.

Comparative Example 4

Selective Impregnation of Molybdenum (Mo) on Zeolite (Beta-Zeolite)

An aqueous solution of ammonium heptamolybdate (0.07 M) was impregnated onto a hydrogen form of beta-zeolite having a silica/alumina molar ratio (SAR) of 13, followed by drying at 150° C. for 10 hours and subsequently calcining at 500° C. for 3 hours.

The molybdenum-supported beta-zeolite thus prepared was mixed with pseudoboehmite to prepare a cylindrical shape with a diameter of 1.6 mm and a length of 3 mm, and after the shaping, the catalyst extrudate was dried at 150° C. for 10 hours, and subsequently fired at 500° C. for 3 hours, thereby preparing a catalyst body.

In the catalyst prepared by the above-described method, the content of beta-zeolite was controlled to be 80 wt % in the mixed support excluding molybdenum and the amount of molybdenum supported was controlled to be 2.0 parts by weight on the basis of the total of 100 parts by weight of the beta-zeolite/inorganic binder (mixed support).

Thereafter, a sulfidation treatment was carried out by the same method as in Comparative Example 1, and the results are shown in Table 2 below.

Example 2

Selective Supporting of Molybdenum (Mo) on Binder

An aqueous solution of ammonium heptamolybdate (0.5 M) was first impregnated onto pseudoboehmite as an inorganic binder, followed by drying at 120° C. for 2 hours, and then mixed with a hydrogen form of beta-zeolite having a silica/alumina molar ratio (SAR) of 13 to prepare a catalyst extrudate having a cylindrical shape with a diameter of 1.6 mm and a length of 3 mm. The catalyst extrudate was dried at 150° C. for 10 hours, and subsequently fired at 500° C. for 3 hours, thereby preparing a catalyst body.

In the catalyst prepared by the above-described method, the content of beta-zeolite was controlled to be 80 wt % in the mixed support excluding molybdenum and the amount of molybdenum supported was controlled to be 2.0 parts by weight on the basis of the total of 100 parts by weight of the beta-zeolite/inorganic binder (mixed support).

Thereafter, a sulfidation treatment was carried out by the same method as in Comparative Example 1, and the results are shown in Table 2 below.

TABLE 2

| | Comparative Example 4 | Example 2 |
|---|---|---|
| Mo supporting | Selective supporting on zeolite | Selective supporting on binder |
| Reaction temperature (° C.) | 350 | 339 |
| Conversion (%) | 44.8 | 44.9 |
| Xylene yield (wt %) | 34.12 | 35.10 |
| Aromatic loss (mol %) | 1.22 | 0.51 |

According to the above table, compared with Comparative Example 4, Example 2 showed similar conversion even at lower reaction temperatures, and the catalyst having a molybdenum (Mo) metal selectively supported on the binder (Example 2) was better than the catalyst having a molybdenum (Mo) metal selectively supported on zeolite (Comparative Example 4) in terms of the xylene yield. Particularly, it was confirmed that the use of the catalyst according to Example 2 showed a significant decrease in aromatic loss.

Comparative Example 5

Selective Impregnation of Molybdenum (Mo) on ZSM-12

An aqueous solution of ammonium heptamolybdate (0.07 M) was impregnated onto a hydrogen form of ZSM-12 zeolite having a silica/alumina molar ratio (SAR) of 25, followed by drying at 150° C. for 10 hours and subsequently calcining at 500° C. for 3 hours.

The molybdenum-supported ZSM-12 zeolite thus prepared was mixed with pseudoboehmite to prepare a extruded body having a cylindrical shape with a diameter of 1.6 mm and a length of 3 mm. The catalyst extrudate was dried at 150° C. for 10 hours, and subsequently fired at 500° C. for 3 hours, thereby preparing a catalyst body.

In the catalyst prepared by the above-described method, the content of ZSM-12 was controlled to be 80 wt % in the mixed support excluding molybdenum and the amount of molybdenum supported was controlled to be 2.0 parts by weight on the basis of the total of 100 parts by weight of the ZSM-12/inorganic binder (mixed support).

Thereafter, a sulfidation treatment was carried out by the same method as in Comparative Example 1, and the results are shown in Table 3 below.

Example 3

Selective Supporting of Molybdenum (Mo) on Binder

An aqueous solution of ammonium heptamolybdate (0.5 M) was first impregnated onto pseudoboehmite as an inorganic binder, followed by drying at 120° C. for 2 hours, and then mixed with a hydrogen form of ZSM-12 having a silica/alumina molar ratio (SAR) of 25 to prepare a catalyst extrudate having a cylindrical shape with a diameter of 1.6 mm and a length of 3 mm. The catalyst extrudate was dried at 150° C. for 10 hours, and subsequently fired at 500° C. for 3 hours, thereby preparing a catalyst body.

In the catalyst prepared by the above-described method, the content of ZSM-12 was controlled to be 80 wt % in the mixed support excluding molybdenum and the amount of molybdenum supported was controlled to be 2.0 parts by weight on the basis of the total of 100 parts by weight of the ZSM-12/inorganic binder (mixed support).

Thereafter, a sulfidation treatment was carried out by the same method as in Comparative Example 1, and the results are shown in Table 3 below.

TABLE 3

| | Comparative Example 5 | Example 3 |
|---|---|---|
| Mo Supporting | Selective supporting on zeolite | Selective supporting on binder |
| Reaction temperature (° C.) | 378 | 362 |
| Conversion (%) | 44.9 | 44.8 |
| Xylene yield (wt %) | 34.32 | 35.30 |
| Aromatic loss(mol %) | 1.02 | 0.40 |

According to the above table, compared with the catalyst having the molybdenum (Mo) metal selectively supported on zeolite (ZSM-12) (Comparative Example 5), Example 3 showed a similar conversion even at a temperature 16° C. lower and was excellent in terms of a xylene yield. Particularly, it was confirmed that the use of the catalyst according to Example 3 showed an aromatic loss reduced to a significantly lower level.

Comparative Example 6

Rhenium (Re) Impregnation after Preparation of Mixed Support (ZSM-5/MOR/Alumina)

A catalyst was prepared by the same method as in Comparative Example 1 except that an aqueous solution of ammonium perrhenate (0.06 M) was used instead of the aqueous solution of ammonium heptamolybdate. Herein, the amount of rhenium was controlled to be 0.6 parts by weight on the basis of the total of 100 parts by weight of the mordenite/ZSM-5/inorganic binder (mixed support), and the percentages of mordenite and ZSM-5 in the mixed support excluding rhenium were controlled to be 60 wt % and 25 wt %, respectively.

A sulfidation treatment was carried out by the same method as in Comparative Example 1. A feedstock composed of 85 wt % of a C7-aromatic fraction containing toluene as a main component and 15 wt % of a C9+ aromatic fraction containing a C9 aromatic as a main component was introduced. While 0.135 cc/m of the feedstock was allowed to flow, a disproportionation/transalkylation reaction was performed. The results are shown in Table 4.

Example 4

Selective Supporting of Rhenium (Re) on Binder

A catalyst was prepared by the same method as in Example 1 except that an aqueous solution of ammonium perrhenate (0.45 M) was used instead of the aqueous solution of ammonium heptamolybdate. Herein, the amount of rhenium was controlled to be 0.6 parts by weight on the basis of the total of 100 parts by weight of the mordenite/ZSM-5/inorganic binder (mixed support), and the percentages of mordenite and ZSM-5 in the mixed support excluding rhenium were controlled to be 60 wt % and 25 wt %, respectively.

A sulfidation treatment was carried out by the same method as in Comparative Example 6, and the results are shown in Table 4 below.

TABLE 4

| | Comparative Example 6 | Example 4 |
|---|---|---|
| Mo supporting | Supporting after mixed support shaping | Selective supporting on binder |
| Reaction temperature (° C.) | 349 | 336 |
| Conversion (%) | 44.8 | 45.1 |
| Xylene yield (wt %) | 28.10 | 29.05 |
| Aromatic loss(mol %) | 1.06 | 0.35 |

According to the above table, compared with the catalyst obtained by preparing a mixed catalyst extrudate and then supporting rhenium (Re) thereon (Comparative Example 6), Example showed a similar conversion even at a lower reaction temperature and was also excellent in terms of a xylene yield. Particularly, it was confirmed that the use of the catalyst according to Example 4 showed an aromatic loss reduced to a significantly lower level.

Comparative Example 7

Pt/Sn Co-Mulling

A catalyst was prepared by the same method as in Comparative Example 2 except that the aqueous solution of ammonium heptamolybdate was changed into an aqueous solution of $H_2PtCl_6$ (0.01 M) and an aqueous solution of $SnCl_2$ (0.08 M). Herein, the amounts of Pt and Sn were respectively controlled to be 0.025 parts by weight and 0.2 parts by weight on the basis of the total of 100 parts by weight of the mordenite/ZSM-5/inorganic binder (mixed support), and the percentages of mordenite and ZSM-5 in the mixed support excluding Pt and Sn were controlled to be 60 wt % and 25 wt %, respectively.

A fixed bed continuous reactor was charged with 2.0 g of the prepared catalyst body as above, and the atmosphere in the reactor was replaced with nitrogen, and then the pressure in the reactor was raised to 30 kg/$cm^2$. Thereafter, nitrogen was replaced with hydrogen, and the atmosphere was maintained at 150° C. for 10 hours while 82 cc/min of hydrogen was allowed to flow, and then the atmosphere was further maintained at 400° C. for 2 hours, thereby carrying out a reduction treatment, and then the reaction was performed by the same method as in Comparative Example 6. The reaction results are shown in Table 5.

Example 5

Selective Supporting of Pt/Sn on Binder

A catalyst was prepared by the same method as in Example 1 except that the aqueous solution of ammonium heptamolybdate was changed into an aqueous solution of $H_2PtCl_6$ (0.03 M) and an aqueous solution of $SnCl_2$ (0.25 M). Herein, the amounts of Pt and Sn were respectively controlled to be 0.025 parts by weight and 0.2 parts by weight on the basis of the total of 100 parts by weight of the mordenite/ZSM-5/inorganic binder (mixed support), and the percentages of mordenite and ZSM-5 in the mixed support excluding Pt and Sn were controlled to be 60 wt % and 25 wt %, respectively.

A reduction treatment was carried out by the same method as in Comparative Example 7, and the results are shown in Table 5 below.

TABLE 5

| | Comparative Example 7 | Example 5 |
|---|---|---|
| Pt/Sn supporting | Co-mulling | Selective supporting on binder |
| Reaction temperature (° C.) | 344 | 330 |
| Conversion (%) | 44.7 | 45.0 |
| Xylene yield (wt %) | 28.12 | 29.02 |
| Aromatic loss(mol %) | 1.07 | 0.50 |

According to the above table, compared with the co-mulled catalyst (Comparative Example 7), Example 5 showed a similar conversion even at a low reaction temperature and was excellent in terms of a xylene yield. Especially, Example 5 showed a significantly reduced result in terms of aromatic loss.

Comparative Example 8

Impregnation of Molybdenum (Mo) on Mixed Support (ZSM-5/Alumina)

An ammonium form of ZSM-5 having a silica/alumina molar ratio of 30 was mixed with an alumina binder, and the mixture was extruded into a cylindrical shape with a diameter of 1.6 mm and a length of 3 mm, followed by drying at 150° C. for 10 hours and subsequently calcining at 500° C. for 3 hours.

Then, an aqueous solution of ammonium heptamolybdate (0.09 M) was impregnated onto the mixed support, followed by drying at 150° C. for 10 hours and then calcining at 500° C. for 3 hours, to thereby prepare a catalyst body.

In the prepared catalyst, the weight percentage of ZSM-5 was controlled to be 70 wt % in the mixed support excluding molybdenum and the amount of molybdenum supported was controlled to be 3.0 parts by weight on the basis of the total of 100 parts by weight of the ZSM-5/inorganic binder (mixed support).

The catalyst was charged by the same method as in Comparative Example 1, followed by a sulfidation treatment. Then, a xylene isomerization reaction was performed on a C8 aromatic compound mixture, as a reactant, composed of 90 wt % of mixed xylene containing ortho-xylene and meta-xylene with para-xylene removed therefrom and 10 wt % of ethyl benzene. The results are shown in Table 6 below.

Comparative Example 9

Selective Impregnation of Molybdenum (Mo) on ZSM-5

An aqueous solution of ammonium heptamolybdate (0.10 M) was impregnated onto an ammonium form of ZSM-5 having a silica/alumina molar ratio (SAR) of 30, followed by drying at 150° C. for 10 hours and subsequently calcining at 500° C. for 3 hours. The molybdenum-supported ZSM-5 thus prepared was mixed with pseudoboehmite to prepare a catalyst extrudate having a cylindrical shape with a diameter of 1.6 mm and a length of 3 mm. The catalyst extrudate was dried at 150° C. for 10 hours, and subsequently fired at 500° C. for 3 hours, thereby preparing a catalyst body.

In the catalyst prepared by the above-described method, the weight percentage of ZSM-5 was controlled to be 70 wt % in the mixed support excluding molybdenum and the amount of molybdenum supported was controlled to be 3.0 parts by weight on the basis of the total of 100 parts by weight of the ZSM-5/inorganic binder (mixed support).

Thereafter, a sulfidation treatment and a xylene isomerization reaction were carried out by the same methods as in Comparative Example 8, and the results are shown in Table 6 below.

Example 6

Selective Supporting of Molybdenum (Mo) on Binder

An aqueous solution of ammonium heptamolybdate (0.75 M) was first impregnated onto pseudoboehmite as an inorganic binder, followed by drying at 120° C. for 2 hours, and then mixed with an ammonium form of ZSM-5 having a silica/alumina molar ratio (SAR) of 30, and the mixture was shaped into a catalyst extrudate having a cylindrical shape with a diameter of 1.6 mm and a length of 3 mm. The catalyst extrudate was dried at 150° C. for 10 hours, and subsequently fired at 500° C. for 3 hours, thereby preparing a catalyst body.

In the catalyst prepared by the above-described method, the weight percentage of ZSM-5 was controlled to be 70 wt % in the mixed support excluding molybdenum and the amount of molybdenum supported was controlled to be 3.0 parts by weight on the basis of the total of 100 parts by weight of the ZSM-5/inorganic binder (mixed support). Thereafter, a sulfidation treatment and a xylene isomerization reaction were carried out by the same methods as in Comparative Example 8, and the results are shown in Table 6 below.

The ethyl benzene conversion and xylene loss in the xylene isomerization were calculated by Equations 4 and 5 below, respectively.

Ethyl benzene conversion (%)=[1−(content of ethyl benzene in produced fraction, %/content of ethyl benzene in fed fraction, %]*100 [Equation 4]

Xylene loss (wt %)=[1−(content of xylene in produced fraction, %)/(content of xylene in fed fraction, %)]*100 [Equation 5]

TABLE 6

| | Comparative Example 8 | Comparative Example 9 | Example 6 |
|---|---|---|---|
| Mo supporting | Supporting after mixed support shaping | Selective supporting on zeolite | Selective supporting on binder |
| WHSV($hr^{-1}$) | 11 | 11 | 11 |
| $H_2$/HC | 2.0 | 2.0 | 2.0 |
| Reaction pressure ($kgf/cm^2$) | 10 | 10 | 10 |
| Ethylbenzene Conversion (%) | 77.1 | 77.3 | 78.2 |
| Reaction temperature (° C.) | 381 | 390 | 369 |
| Xylene loss (wt %) | 1.3 | 2.1 | 0.49 |

According to the above table, the catalyst having the metal selectively supported on the binder (Example 6), compared with Comparative Example 8 and 9, showed a similar ethyl benzene conversion at a low reaction temperature and showed a significantly reduced result in terms of xylene loss.

As described above, it can be seen that catalysts having an active metal selectively supported on only an inorganic oxide binder, like the examples, showed high catalytic activity in the preparation of C8 aromatics (especially, xylenes) through a disproportionation/transalkylation/dealkylation reaction of aromatic hydrocarbons and the production of para-xylene through an isomerization reaction of C8 aromatics (especially, mixed xylenes). It was confirmed that the catalysts like the examples significantly reduced aromatic loss or xylene loss, which affects the yield of xylenes or para-xylene in a product, compared with catalysts having an active metal supported on zeolite or a mixed support of zeolite and a binder, or catalysts prepared by co-mulling of an active metal together with zeolite and a binder.

Accordingly, it should be understood that simple modifications and variations of the present disclosure may be easily used by those skilled in the art, and such modifications or variations may fall within the scope of the present disclosure.

What is claimed is:

1. A method for producing C8 aromatics, the method comprising:

providing a feedstock containing benzene, toluene, and/or C9+ aromatics; and forming a reaction product containing an increased amount of C8 aromatic hydrocarbons from the feedstock by at least one of disproportionation, transalkylation, and dealkylation reactions in the presence of a catalyst, wherein the catalyst comprises:

(A) a mixed support comprising: (i) a first zeolite, which has a silica-alumina ratio (SAR) of 5 to 300 and a 10-membered ring pore structure, and/or a second zeolite, which has a silica-alumina ratio (SAR) of 5 to 300 and a 12-membered ring pore structure with a pore diameter of 6 to 9 Å; and (ii) a refractory inorganic oxide binder; and (B) a first metal supported only on the refractory inorganic oxide binder in the mixed support and having hydrogenation activity, wherein the first metal is at least one selected from the group consisting of platinum (Pt), tungsten (W), rhenium (Re), ruthenium (Ru), iridium (Jr), nickel (Ni), palladium (Pd), and molybdenum (Mo), wherein the amount of the first metal supported is in a range of 0.01 to 5 wt % on the basis of the weight of the mixed support, and wherein the aromatic loss in the reaction product is 1 mol % or less.

2. The method of claim 1, wherein the refractory inorganic oxide is at least one selected from the group consisting of alumina, silica, aluminum phosphate, titania, zirconia, bentonite, kaolin, clinoptilolite, and montmorillonite.

3. The method of claim 1, wherein the first zeolite is at least one selected from the group consisting of ZSM-5, ZSM-11, ZSM-23, ZSM-48, ZSM-57, EU-2, TNU-9, and MCM-22, and the second zeolite is at least one selected from the group consisting of mordenite (MOR), beta-zeolite, ZSM-12, ZSM-10, and ZSM-18.

4. The method of claim 1, wherein the first metal is at least one selected from the group consisting of platinum (Pt), rhenium (Re), and molybdenum (Mo).

5. The method of claim 1, wherein the catalyst further comprises at least one second metal selected from the group consisting of tin (Sn) and lead (Pb), which is supported only on the refractory inorganic oxide binder of the mixed support, the amount of the second metal being in a range of 0.01 to 5 wt % on the basis of the weight of the mixed support.

6. The method of claim 5, wherein the atomic ratio of the first metal:the second metal is in a range of 1:0.5 to 50.

7. The method of claim 1, wherein the first metal is in a reduced form, a partially oxidized form, or a sulfide form.

8. The method of claim 1, wherein the mixed support comprises, on the basis of the weight of the mixed support, 5 to 95 wt % of the first zeolite and 95 to 5 wt % of the refractory inorganic oxide binder.

9. The method of claim 1, wherein the mixed support comprises, on the basis of the weight of the mixed support, 5 to 95 wt % of the second zeolite and 95 to 5 wt % of the refractory inorganic oxide binder.

10. The method of claim 1, wherein the mixed support comprises, on the basis of the weight of the mixed support, 5 to 70 wt % of the first zeolite, 10 to 90 wt % of the second zeolite, and 1 to 70 wt % of the refractory inorganic oxide binder.

11. The method of claim 1, wherein, when the first metal is platinum, it is in a reduced form or a sulfide form, when the first metal is rhenium, it is in a reduced form or a sulfide form, and when the first metal is molybdenum, it is in a partially oxidized form or a sulfide form.

* * * * *